United States Patent [19]
Dall et al.

[11] Patent Number: 5,665,089
[45] Date of Patent: Sep. 9, 1997

[54] BONE FIXATION SYSTEM

[76] Inventors: Desmond Meiring Dall, 2470 Inverness Ave., Los Angeles, Calif. 90033; Anthony William Miles, Tremont, 14 Upper Oldfield Park, Bath BA2 3JZ, United Kingdom; Hans Friedrich Schmotzer, Gartenstrasse 7, CH-6330 Cham, Switzerland

[21] Appl. No.: 302,883

[22] PCT Filed: Mar. 19, 1993

[86] PCT No.: PCT/GB93/00566

§ 371 Date: Nov. 21, 1994

§ 102(e) Date: Nov. 21, 1994

[87] PCT Pub. No.: WO93/18716

PCT Pub. Date: Sep. 30, 1993

[30] Foreign Application Priority Data

Mar. 19, 1992 [GB] United Kingdom ............ 9206018

[51] Int. Cl.$^6$ ............................................. A61B 12/80
[52] U.S. Cl. .................... 606/71; 606/70; 606/73; 606/74
[58] Field of Search ................ 606/69, 70, 71, 606/74, 72, 73, 60, 103

[56] References Cited

U.S. PATENT DOCUMENTS

| | | |
|---|---|---|
| 3,604,414 | 9/1971 | Borges . |
| 4,119,091 | 10/1978 | Partridge .......... 606/69 |
| 4,943,292 | 7/1990 | Foux .............. 606/69 |
| 5,041,114 | 8/1991 | Chapman et al. ...... 606/69 |
| 5,087,260 | 2/1992 | Fixel ............. 606/69 |
| 5,190,545 | 3/1993 | Corsi et al. ....... 606/74 |
| 5,269,784 | 12/1993 | Mast ............. 606/71 |
| 5,344,421 | 9/1994 | Crook ............ 606/70 |

FOREIGN PATENT DOCUMENTS

| | | |
|---|---|---|
| 048038 | 3/1982 | European Pat. Off. . |
| 242267 | 10/1987 | European Pat. Off. . |
| 347658 | 12/1989 | European Pat. Off. . |
| 438428 | 12/1911 | France . |
| 2357229 | 2/1978 | France . |
| 4212635 | 12/1992 | Germany . |
| 335797 | 3/1959 | Switzerland . |
| 373516 | 1/1964 | Switzerland . |
| 1173480 | 12/1969 | United Kingdom . |
| 90/04366 | 5/1990 | WIPO . |

*Primary Examiner*—Guy V. Tucker
*Attorney, Agent, or Firm*—Larson and Taylor

[57] ABSTRACT

A cerclage fixation component and a screw fixation component are engageable together to form a composite bone fixation device. The cerclage component may be a ladder plate with openings defined between bridges. The openings provide sockets for bosses of the screw fixation component.

21 Claims, 5 Drawing Sheets

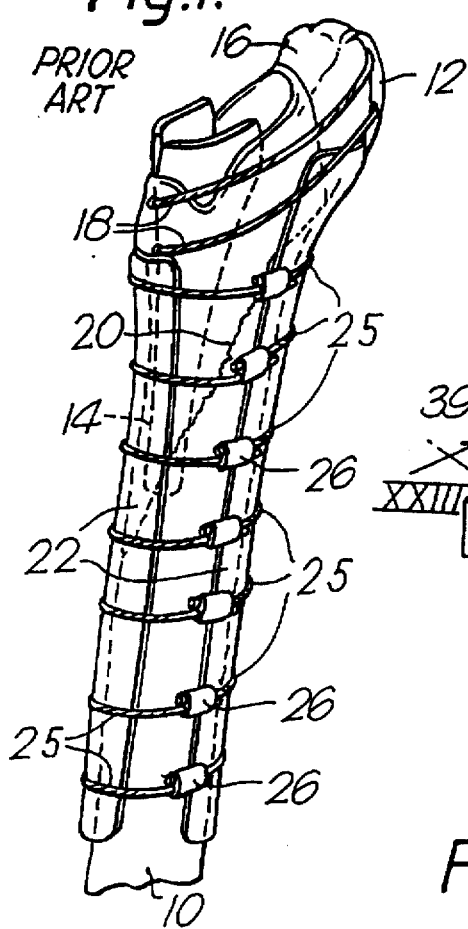
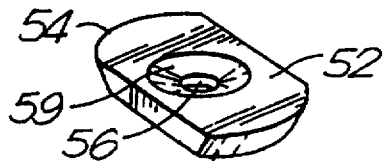
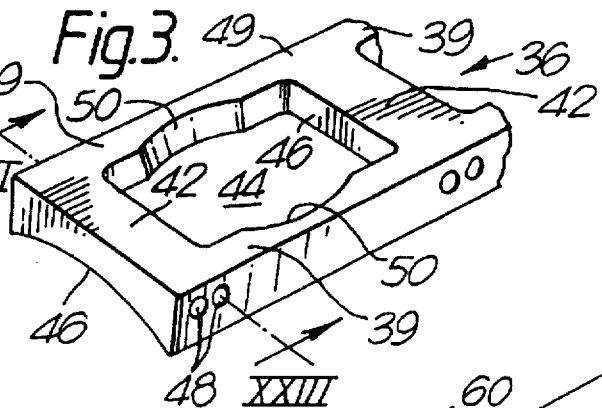
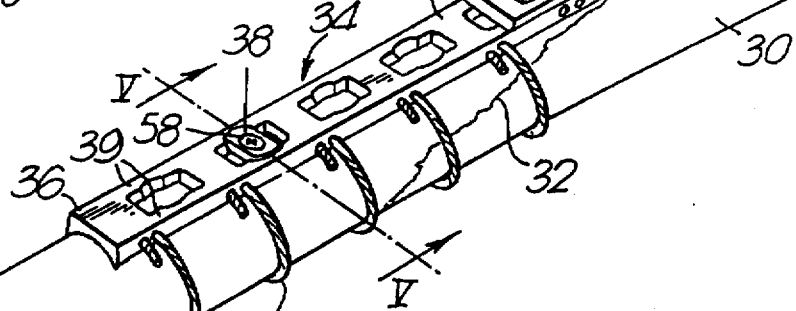
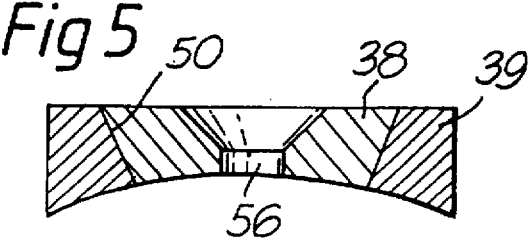
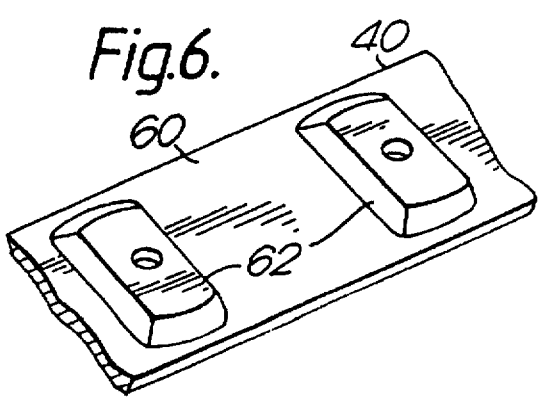

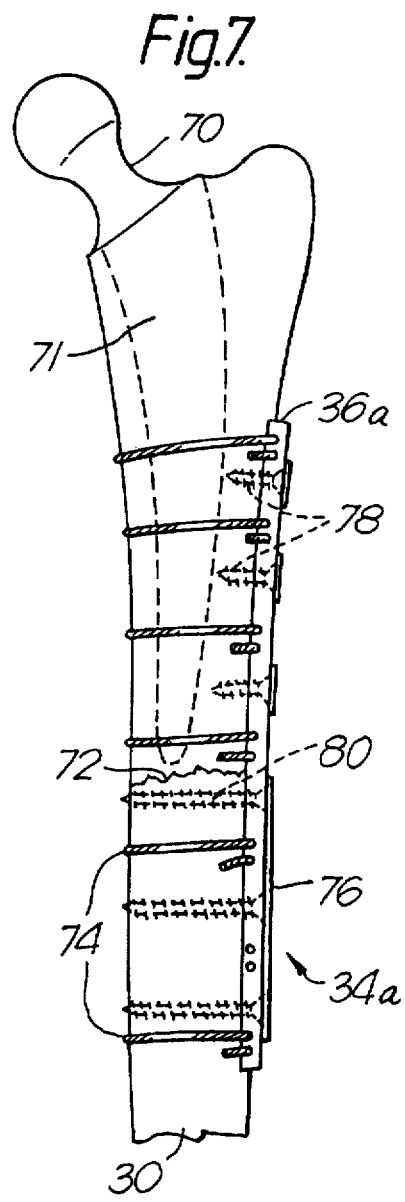
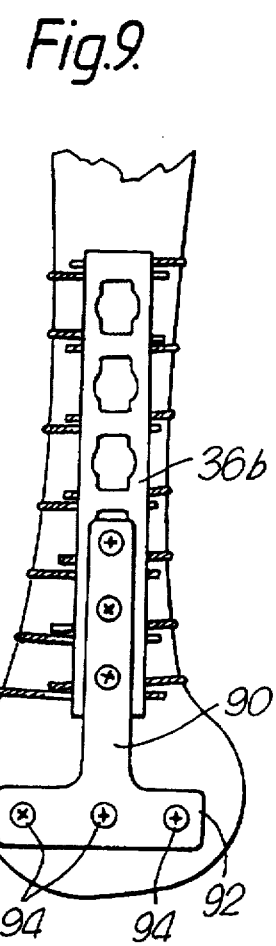
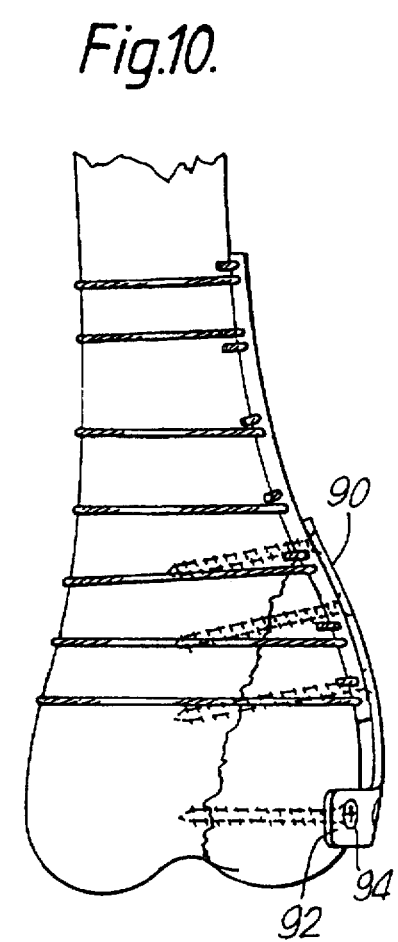
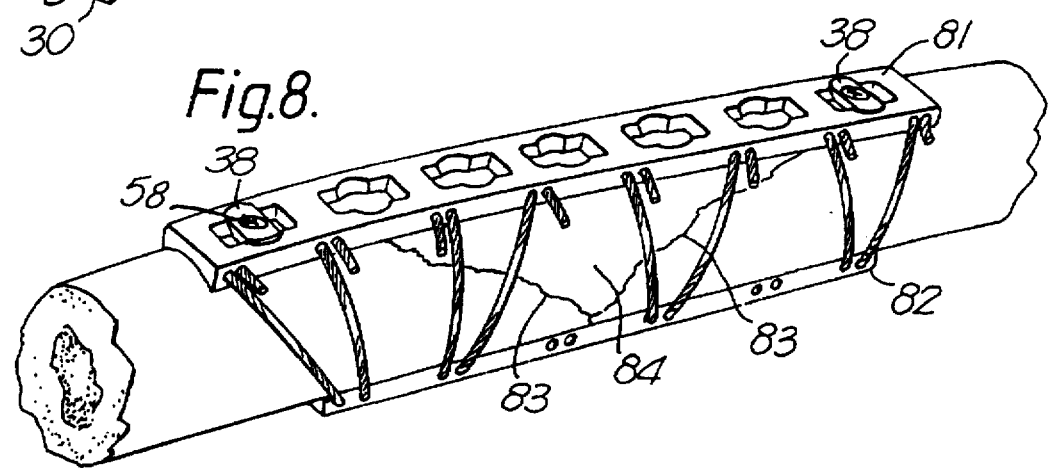

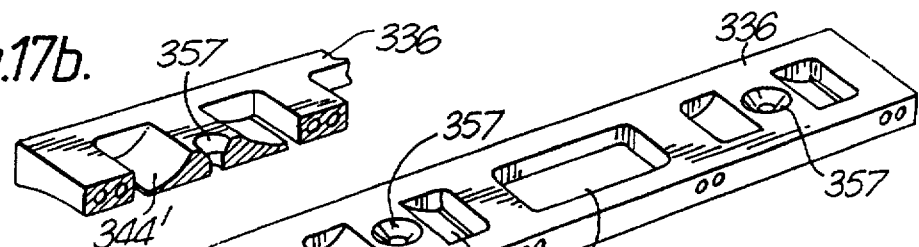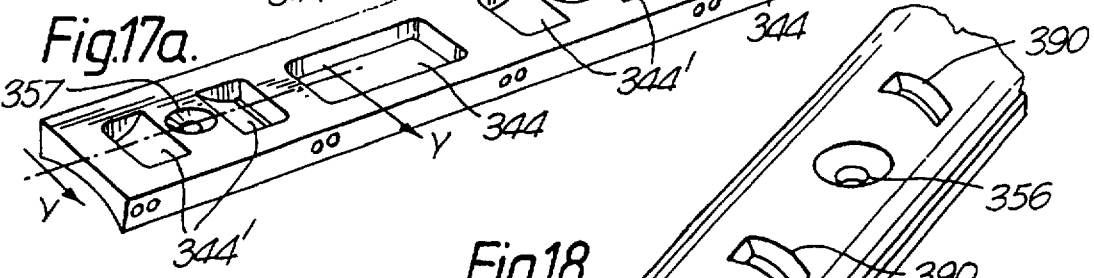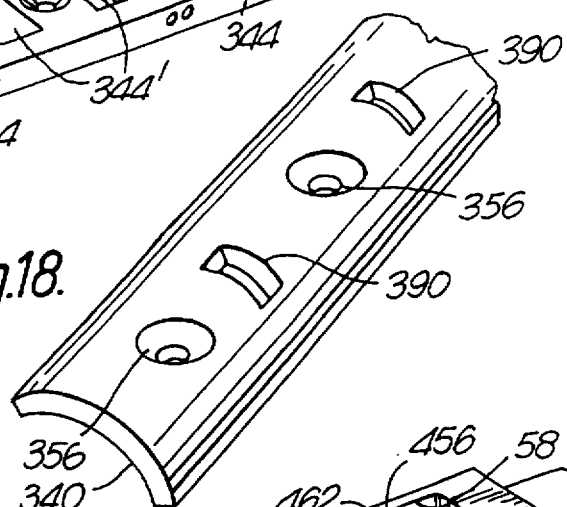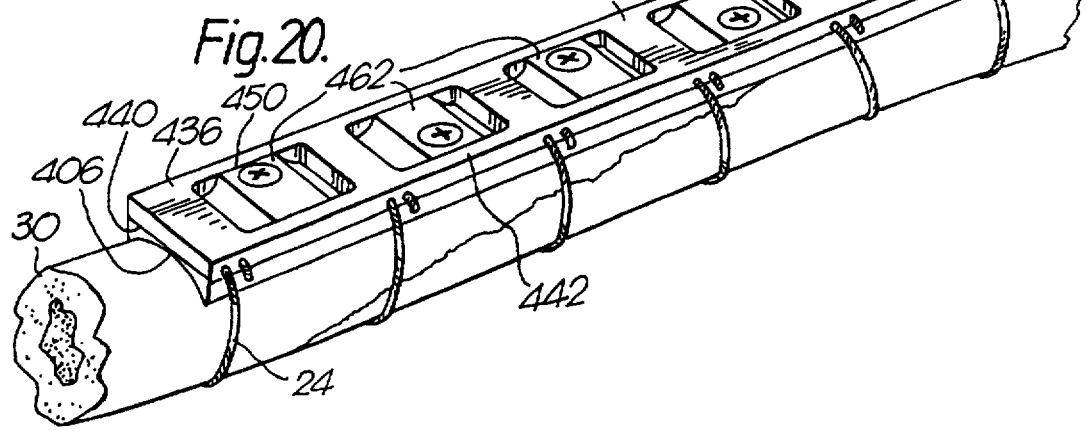

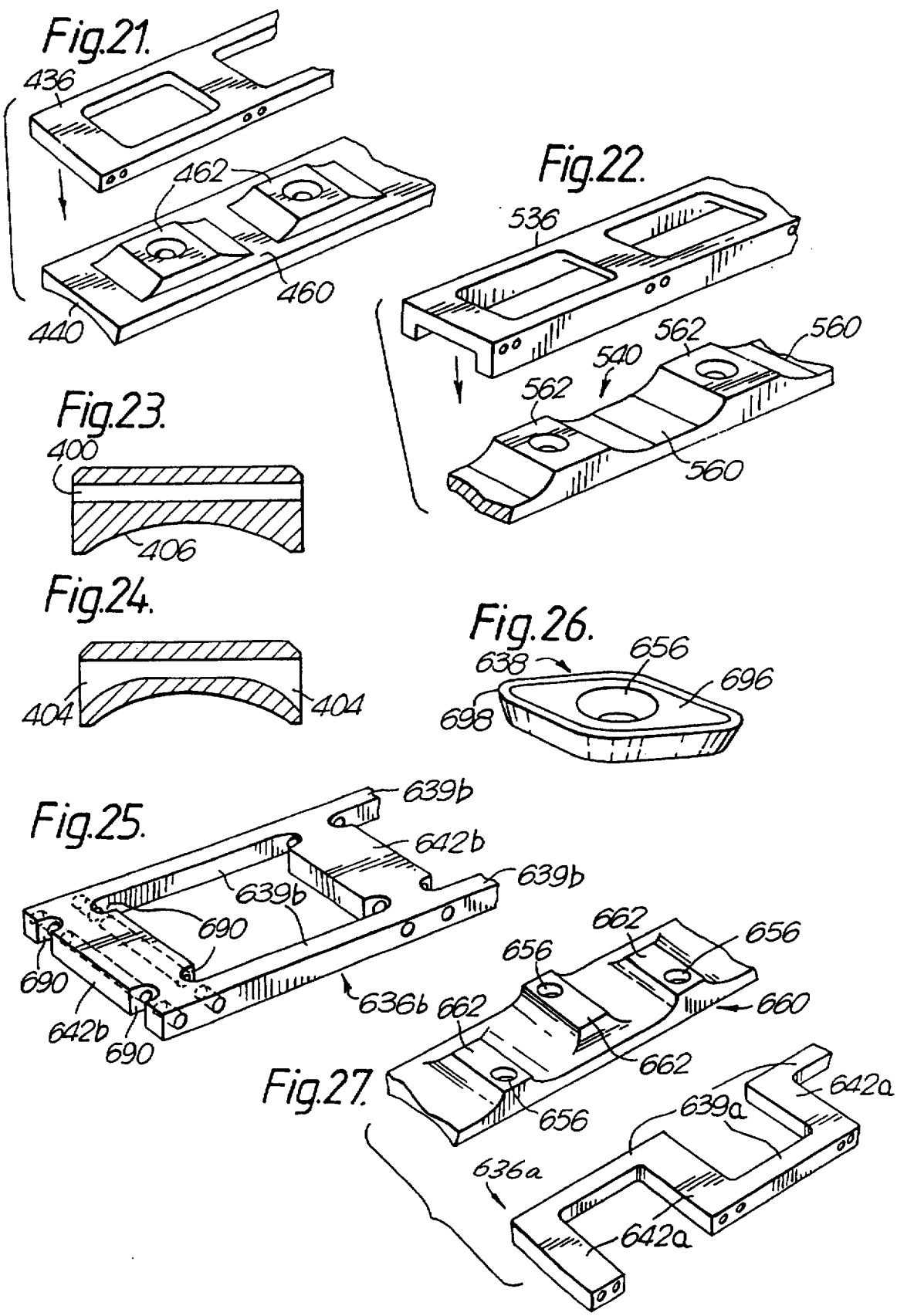

BONE FIXATION SYSTEM

This application is filed under 35 U.S.C. 371 based on PCT/GB93/00566 which was filed on Mar. 19, 1993.

TECHNICAL FIELD

The present invention relates to a bone fixation system, and particularly (though not exclusively) to a system that may be employed in bone implant surgery such as hip replacement operations, or subsequent surgical treatment of the bone structure in the region of an implant. The term 'bone fixation' is intended to cover not only the connection of bone to bone but also the connection of components to bone.

BACKGROUND ART

Cerclage is a known fixation technique in which a bone is encircled by a flexible member such as a cable which is drawn tight and clamped. This may serve to hold portions of bone or bone graft together and/or to retain some surgically applied component. For an account of current cable techniques for trochanteric reattachment, femoral allograft fixation and fractures of the proximal femur in revision total hip arthroplasty, the reader is referred to D. M. Dall, *Techniques in Orthop.* 1991; 6(3):7–16. This describes, among other things, use of a bone fastener for the greater trochanter, as disclosed in U.S. Pat. No. 4,269,180. This known bone fastener is a generally H-shaped implant comprising a base structure including a pair of limbs joined by a bridge, the bridge being bounded by a front face, a rear face and edge faces, a plurality of teeth protruding from the base structure, all the teeth lying on the same side of the base structure, and at least one hole in the base structure for receiving a cable, the hole being elongate in form, extending lengthways through the bridge, and being open at each end. The bridge is adapted to be crimped so that cable(s) can be passed through the hole(s), pulled tight, and then locked by crimping.

FIG. 1 is a drawing, taken from the cited paper, showing a femur 10 that has undergone reconstructive surgery including use of a fastener 12 according to U.S. Pat. No. 4,269,180. In this procedure, the greater trochanter 16 was cut (osteotomised) to facilitate installation in the bone cavity of an internal bone graft 14 and the stem of a prosthesis (not shown but corresponding to stem 71 in FIG. 7). Thereafter the greater trochanter 16 was reattached to the femur 10 by means of the fastener 12 and cerclage cables 18. In addition a fracture 20 of the femur was surgically treated with a further application of cerclage techniques. Thus elongate medial and lateral bone grafts 22 have been applied to the bone, and bound in place by a multiplicity of cerclage cables 25, each of which has been drawn tight and had its ends locked by crimping in an individual crimp sleeve 26.

A disadvantage of cerclage fixation is that it tends to provide relatively little resistance to some forms of displacement, e.g. relative rotation of components and/or portions of bone and/or bone grafts encircled by cerclage cables. Furthermore some shapes and locations are not well suited to cerclage. A second technique involves screws, which are screwed into bone. A screwed connection is commonly quite good at resisting relative displacement such as rotation. But particularly where the bone is weak, e.g. being spongy, a screwed connection will be of low mechanical strength. Furthermore, if screwing were to be substituted for cerclage for securing the bone grafts 22 shown in FIG. 1, there would be a problem in the upper region, in that only short screws could be used since otherwise they would meet the stem which is typically of metal. Thus cerclage and screw fixation each have advantages and disadvantages, and it would be desirable to have a system that made the advantages of both available.

DISCLOSURE OF INVENTION

According to the present invention there is provided a bone fixation system comprising first and second fixation means each having at least one fixation element receiving means, wherein said first fixation means comprises a cerclage fixation means, having a body which defines at least one passage for a cerclage cable and has deformable portions which are deformable to crimp a cerclage cable in said passage, said passage constituting a said fixation element receiving means; and said second fixation means comprises a screw fixation means having at least one screw receiving opening constituting a said fixation element receiving means; said first and second fixation means having complementary mutual engagement formations so that they can be located together to form a composite fixation means capable of fixation by means of both at least one cerclage cable and at least one screw.

Preferably at least one of the first and second fixation means is elongate and has a plurality of fixation element securement means. Preferably an elongate fixation means has a plurality of engagement formations along its length, so that a complementary engagement formation of another fixation means is selectively engageable at plural locations.

In one preferred type of embodiment, the cerclage fixation means comprises a ladder body comprising a pair of elongate side limbs bridged by a plurality of longitudinally spaced bridges. The bridges may provide the cerclage cable passages and deformable crimping portions. There are openings defined between adjacent bridges, and portions of the side limbs, and the limb portions are shaped to provide complementary engagement formations for screw fixation means. Thus a screw fixation means may comprise a shaped, e.g. tapered, boss, and the side limb portions of the ladder body may provide a complementarily shaped recess.

In another aspect the invention provides a kit of parts comprising a multiplicity of first and second fixation means, whereby a range of composite fixation means can be provided.

In a third aspect the invention provides a cerclage fixation means (which may be usable in a composite fixation means as defined above), comprising an elongate ladder member having respective elongate side portions at both lateral sides, and a multiplicity of bridge portions connecting side portions, adjacent bridge portions being spaced so as to define openings; there being through-holes for cerclage cables extending across the ladder member through at least some of the bridge portions. Such a ladder member may have means for receiving fixing screws. These may be apertured portions for receiving screws directly and/or formations (e.g. sockets) in which screw receiving means are engageable.

In a fourth aspect the invention provides a method of connecting or supporting an article or assembly (preferably comprising a bone) which comprises connecting thereto a fixation means provided by the invention according to the first, second or third aspect.

Some embodiments of the present invention will now be described in more detail by way of example with reference to the accompanying drawings.

BRIEF DESCRIPTION OF DRAWINGS

FIG. 1 is a perspective view of a bone structure with bone fixation elements of the prior art;

FIG. 2 is a perspective view of a fractured bone with fixation elements according to a first embodiment of the present invention;

FIG. 3 is a perspective view on a larger scale of a part of a ladder plate of the first embodiment;

FIG. 4 is a perspective view of a single-screw fixation means of the first embodiment;

FIG. 5 is a section on V—V in FIG. 2;

FIG. 6 is a perspective view from beneath of a part of a many-screw fixation means of the first embodiment;

FIG. 7 shows a practical application of the first embodiment in treating a femur which has a fracture at the tip of the prosthetic stem;

FIG. 8 is a perspective view showing another practical application to treat a complex fracture with a butterfly fragment;

FIGS. 9 and 10 are front and side views of a bone structure with a variant of the first embodiment;

FIGS. 15 and 16 are like views of further variants;

FIG. 17a is a top plan view of a ladder plate with screw holes, and FIG. 17b is a section on y—y;

FIG. 18 is a perspective view of another form of elongate fixation means;

FIG. 20 is a view like that of FIG. 2 showing another embodiment;

FIG. 21 shows details of the components of the FIG. 20 embodiment separated;

FIG. 22 is a view like that of FIG. 21 but showing a variant;

FIG. 23 is a section of a ladder plate e.g. as shown in FIG. 3, on XXIII—XXIII;

FIG. 24 is a view similar to that of FIG. 23 showing a modification;

FIG. 25 shows a detail of modified cerclage fixation component; and

FIG. 26 shows a detail of modified screw fixation component; and

FIG. 27 is a view like that of FIG. 21 but showing a further embodiment.

MODES FOR CARRYING OUT THE INVENTION

Figure 11:
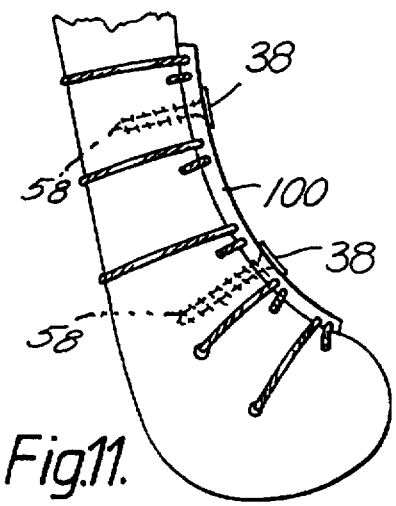
FIG. 11 shows a bone structure with a further variant of the first embodiment.

FIG. 2 shows a bone 30 having a fracture 32. The bone is held together by a composite fixation means 34 comprising a ladder plate 36, a single-screw fixation means 38, and a many-screw fixation means 40. The ladder plate 36 is a unitary body having the form of a pair of side limbs 39 connected by bridges 42 (FIG. 3). Thus there are defined a plurality of openings 44, each approximately rectangular in plan. The underside 46' of the plate 36 is curved to conform to the surface of the bone 30 to which it is to be applied.

Pairs of holes 48 pass through the plate 36 in the region of each bridge 42. (A variant could have single holes.)

Each opening 44 is delimited by an edge 46 that generally extends at right angles to the upper surface 49 of the plate. However, at intermediate regions of the longitudinal portions, there are taper portions 50 which together define an engagement formation delimiting a socket in the opening 44, spaced from the adjacent bridges 42. FIG. 4 shows a single-screw fixation means 38. FIG. 5 shows such a fixation means 38 located in one of the sockets of the ladder plate. The fixation means 28 has a body with a pair of opposed faces 54 that have a complementary taper to the taper portions 50 in the ladder plate 36. The body also has a hole 56 to accommodate the shaft of a screw 58, and a countersunk portion 59 to accommodate the head. (In generally known fashion, the hole and counter-sinking may be relatively large so that a screw can be angled so that its angle of penetration into the bone can be adapted to particular circumstances.) Whereas the width of the fixation means between the tapered faces 54 substantially corresponds to the width of the opening 44, in the longitudinal direction the fixation means is substantially narrower than the opening 44 (in this example being no wider than the longitudinal extent of the taper portions 50). Thus even when the single screw fixation means 38, is located in an opening 44, it is still possible to crimp an adjacent bridge 42 with a crimping tool. Furthermore, distortion of a bridge caused by crimping does not interfere with subsequent location of a (single or many-screw) fixation means.

FIG. 2 also shows a many-screw fixation means 40, whose underside is shown in FIG. 6. It can be seen that it has the form of an elongate plate 60 whose underside has a plurality of bosses 62 each of which has a form substantially corresponding to that of a single-screw fixation means 38. Of course, the spacing of these bosses 62 corresponds to the spacing of the openings 44 in the ladder-plate 36. Thus, as shown in FIG. 2, the many-screw fixation means 40 can be located at a required position along the length of the ladder plate 36.

For practical use, the ladder plate 36 may first be mounted on the bone 30 and secured there by cerclage, the cerclage cables 64 being passed through holes 48. Each loop of cable is pulled tight and then locked in place by crimping a respective bridge 42, in a generally conventional way. Thereafter one or more single-screw and/or many-screw fixation means can be coupled to the ladder plate, and fixed to the bone 30 by means of screws 58. Note that the complementary engagement formations are spaced from the bridges 42, so that the deformation of the bridges associated with the crimping of the cables 64 does not affect the proper seating.

FIG. 7 shows a composite fixation means 34a generally as previously described, applied to a situation similar to that shown in FIG. 1, namely to a femur which has received an implant 70 and subsequently sustained a fracture 72. Thus there is a ladder plate 36a which extends on both sides of the fracture 72 and is secured to the bone 30 by cerclage cable 74. In this particular example, the ladder plate 36a has six openings. The lower three of these are covered by a three-screw fixation means 76, while the upper three contain single-screw fixation means 38 (not shown). These are secured to the bone by means of unicortical screws 78; that is, by relatively short screws that extend only a short way into the central cavity. Thus their use is not prevented by the presence of the shank of the implant 70. Below the implant 70, use is made of bicortical screws 80, which extend diametrically across the bone and engage both cortices.

FIG. 8 shows a seven-opening ladder plate 81 and a five-opening ladder plate 82 used for bracing a complex fracture 83 with a butterfly fragment 84. The end openings of at least the upper ladder plate 81 contain single-screw fixation means 38, which are screwed to the bone.

FIGS. 9 and 10 show a variant in which the many-screw fixation means 90 extends beyond a ladder plate 36b. In this example, it is formed as a T-plate insert. Thus, remote from the ladder plate 36b it has a cross-piece 92 having screw-receiving openings 94. As can be seen from FIG. 10, it is contoured to embrace the bone, in this case being adapted for treatment of a supracondylar fracture.

As shown in FIG. 11, it is also possible to use a contoured ladder plate 100 (in this example, in conjunction with two single-screw fixation means 38).

Figure 12:
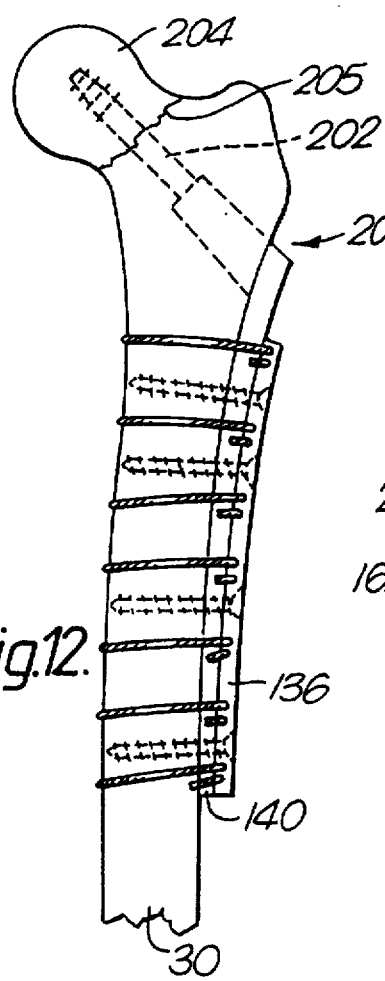
FIG. 12 is a side elevation of a bone structure with fixation elements according to a second embodiment of the invention.
Figure 13:
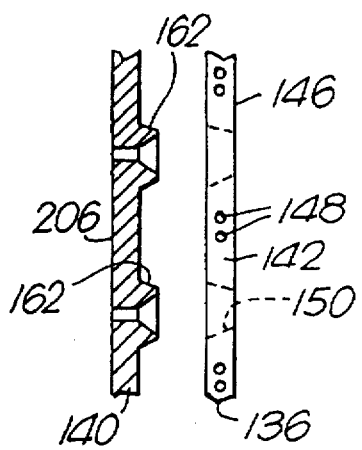
FIG. 13 is a side elevation on a larger scale showing portions of the fixation means of the second embodiment.

FIGS. 12 and 13 show a second type of embodiment differing from those previously described in that the ladder plate 136 is intended to locate over the many-screw fixation means 140, which is located against the bone 30. In the example shown in FIG. 12, the many-screw fixation means 140 also has an additional functionality. Thus it projects beyond the ladder plate 136 and has a generally conventional formation 200 for engaging a sliding hip-screw 202, for use in fixation of the femoral head 204 in a subcapital fracture 205.

Figure 14:
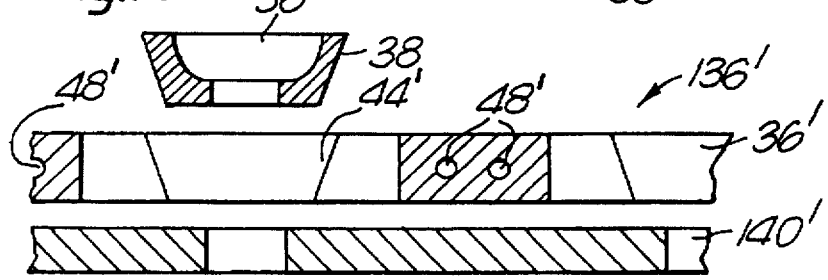
FIG. 14 is a side elevation on a still larger scale showing a variant of the embodiment shown in FIG. 13.
Figure 15:
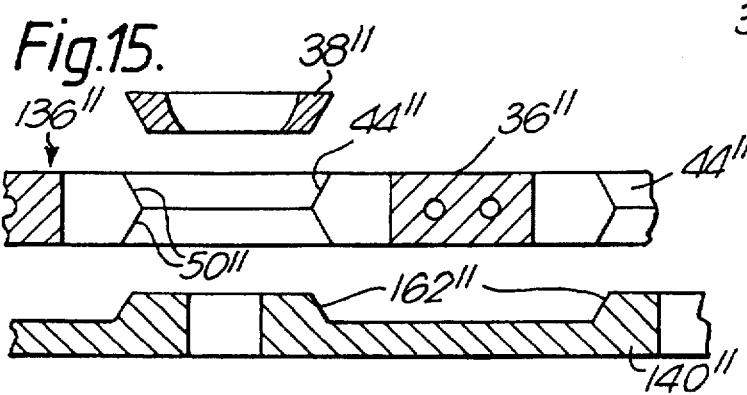

As can be seen from FIG. 13, the many-screw fixation means 140 is generally similar to that shown in FIG. 6, in that it has bosses 162. However, in the intended mode of use, these face away from the bone. The opposite face 206, which lies against the bone, will generally be contoured to fit it. The ladder plate 136 is generally similar to that shown in FIG. 3, notably in having bridges 142, cable holes 148 and openings with taper portions defining sockets 150. But in the intended configuration of use, the sockets enlarge towards the bone, and the opposite face 146 will generally be planar. Particularly when a ladder plate is intended to locate over the screw fixation means, it may be desirable for the ladder plate (or other cerclage component) also to be fixable with screws. Where the two fixation means overlap, they may have screw openings in register. Thus FIG. 14 shows a variant of FIG. 13 in which a ladder plate 136' has at least a portion 36' that resembles the ladder plate 36 shown in FIGS. 2 and 3, with holes 48' and openings 44' that can receive screw plate inserts, e.g. single screw plate inserts 38. The underlying screw plate 140' has holes in register with the screw-holes 56 of the inserts 38 when these are in the openings 44'. Thus screws can be used to connect the ladder plate 136' to the screw plate 140', and to secure both of them to an underlying bone. The screw plate 140' need not then have bosses 162. FIG. 15 shows an alternative in which a ladder plate 136" has a portion 36" with openings 44" with double socket formations 50", widening towards the top and bottom faces. The underlying screw plate 140" then has small bosses 162" for seating in the lower portions of the double sockets; and screw plate inserts 38" seat in the upper portions of the sockets 50".

FIG. 16 shows a further variant in which a screw plate insert 238 has a lower threaded portion 238a for engaging a complementary thread 239 in the underlying screw plate 240. This idea of connecting together the two fixation means can be applied to other forms of fixation means, and can be effected with other forms of connecting element.

FIG. 17 a and b show a variant in which a ladder plate 336 is similar to the plate 36 as shown in FIG. 2, but has screw holes 357. Such a plate may be used on its own or in conjunction with a screw plate. A plate for use on its own may have a multiplicity of screw holes 357. It may then only have small ladder openings 344' since there would be no need for the larger, socket-providing openings 344.

Figure 19:
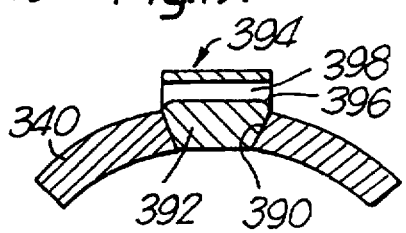
FIG. 19 is a sectional view through an elongate fixation means as shown in FIG. 18 and further showing a sleeve element engaged in a slot.

FIGS. 18 and 19 show another type of embodiment in which an element corresponding to the ladder plate of (e.g.) FIG. 2 is an underlying screw plate 340, having alternating countersunk screw holes 356 and slots 390. The slots, which may have tapered or straight walls, receive mating portions 392 of crimp sleeves 394. These have portions 396 that project from the slots 390 and have through-holes 398. The projecting portions are deformable to crimp a cable in a hole 398 or pair of holes.

FIG. 20 shows a presently preferred embodiment having an elongate cerclage fixation device in the form of a ladder plate 436 (with crimpable bridges 442 and socket portions 450). This engages on top of an elongate screw fixation device 440 which has projecting bosses 462 and a lower face 406 which is curved to lie against the surface of a bone 30. Each boss has an opening 456 for a screw 58. It may be generally desirable for screw openings to be staggered, as shown here, so that the screws do not tend to produce a line of weakness in the bone. Other details are similar to those shown in FIGS. 12 and 13. FIG. 21 shows portions of the devices 436,440 separated. The screw fixation device 440 has a wide base plate 460 which extends laterally beyond the projections 462. The ladder plate 436 is a flat plate of the same width. FIG. 22 shows a variant in which the screw fixation device 540 is relatively narrower, the base plate 560 in the example being of the same width as the projections 562. The cerclage fixation device 536 is channel shaped, so that it locates over and substantially conceals the screw fixation device.

FIG. 27 shows that a ladder plate 636a need not have continuous side portions. It can have staggered short portions 639a connected by bridges 642a. The resulting zigzag plate 636 can embrace bosses 662 on an elongate screw fixation plate 660. The bosses 662 are laterally staggered. Thus the screw openings 656 can also be staggered as is desirable.

Hitherto it has been assumed that holes for cerclage cables are simple uniform bores 400 as shown in FIG. 23. However it may be preferable for a bore to follow an arcuate path, e.g. in parallel with a curved rear surface 406. Alternatively or additionally a bore may have shaped mouths 404 as shown in FIG. 24, to provide a smoother cable path around the bore.

FIG. 25 shows a detail of a cerclage fixing device 636b to illustrate a variant form of crimping bridge. The device 636 has side portions 639b connected by bridges 642b. The bridges 642b have portions of reduced width adjacent the side portions 639b (shown here as due to opposed pairs of scallops 690). This is to facilitate crimping and reduce the risk of cracks at the bridge/side portion junction.

FIG. 26 shows a modified screw plate insert 638. This comprises deformable material to assist seating in a socket of a cerclage fixation device, to reduce fretting, and to allow for deformation when an assembly is secured to a bone.

In this example there is a metal insert 696 in which the screw-hole 656 is defined; and this is set in a plastics liner 698. Of course projecting bosses of long screw-plates (e.g. as shown in FIG. 6) could similarly be formed with plastics liners.

For surgical use, the components must all be made of biocompatible materials. Generally the ladder plates and screw fixation means will be of metal, for example stainless steel, chrome cobalt, or titanium alloy, optionally with liners (as described with reference to FIG. 26) of biocompatible deformable plastics materials. All metal components of a single system (which may include the cable) should be of the same material, or materials which are compatible, to avoid electrolytic effects.

The component which is intended to locate against the bone may have formations to assist gripping to the bone surface, such as serrations or "teeth".

Fixation systems embodying the present invention may be used in human and veterinary surgery. Of course, the same principles will also be applied to connection of elements in other fields.

We claim:

1. A bone fixation system comprising:
   cerclage cables; and
   an elongate unitary body including a top face, a bottom face, a spaced pair of elongate side portions which define an oppositely directed pair of lateral edges, a multiplicity of spaced-apart bridge portions connecting said side portions, said bridge portions each having a pair of oppositely directed side edges shaped so that a plurality of approximately rectangular openings are defined between opposed side edges of adjacent bridge portions, and pairs of through-bores for receiving said cerclage cables disposed therein;
   wherein said pairs of through-bores are located between adjacent approximately rectangular openings and extend through said bridge portions, each of said pairs of through-bores being positioned within said bridge portions such that crimping said side edges of each of said bridge portion substantially closes said pair through-bores to secure said cerclage cable disposed therein;
   wherein said elongate unitary body is adapted to be located with said bottom face overlying a bone and fixed thereto by passing said cerclage cable around the bone and through one of said pairs of through-bores, pulling the cable tight, and locking it in place by crimping the bridge through which said through-bores pass.

2. A bone fixation system as in claim 1 further comprising a screw fixation means for bridging broken bones which is affixed to bone by at least one screw having at least one screw receiving opening; said cerclage receiving means and said screw fixation means having complementary mutual engagement formations so that they can be located together to form a composite fixation means capable of fixation by means of both at least one cerclage cable and at least one screw.

3. A bone fixation system according to claim 2 wherein said screw fixation means is elongate and has a plurality of said screw receiving openings.

4. A bone fixation system according to claim 3 wherein at least one of said cerclage receiving means and screw fixation means is elongate and has a plurality of engagement formations along its length, so that a complementary engagement formation of another fixation means is selectively engageable at plural locations.

5. A bone fixation system according to claim 2 wherein said side portions of the elongate ladder member are shaped to provide complementary engagement formations for said screw fixation means in said openings.

6. A bone fixation system according to claim 5 wherein said screw fixation means comprises a shaped boss, and said side portions of the elongate ladder member provide a complementarily shaped recess.

7. A bone fixation system according to claim 6 wherein the boss and recess are dimensioned so that the recess and the boss when engaged therein are spaced from the adjacent bridge portions.

8. A bone fixation system according to claim 6 wherein the screw fixation means is elongate with a plurality of screw-receiving bosses along its length.

9. A bone fixation system according to claim 2 wherein the screw fixation means is elongate, having a first portion for engaging the cerclage fixing means and a second portion for extending beyond the cerclage receiving means and being adapted for connection to bone or to a bone implant.

10. A bone fixation system according to claim 2 wherein the cerclage receiving means has a first major face which is contoured for lying against bone, and an oppositely-facing second major face at which the screw fixation means is applied to engage the engagement formations.

11. A bone fixation system according to claim 2 wherein the screw fixation means has a first major face which is contoured for lying against bone, and an oppositely-facing second major face at which the cerclage receiving means is applied to engage the engagement formations.

12. A bone fixation system according to claim 2 wherein the cerclage receiving means also has means for screw fixation.

13. A bone fixation system according to claim 2, wherein said first screw fixation means is elongate with a plurality of engagement means; at least one second screw fixation means comprising at least one shaped boss; and a cerclage receiving means which is elongate and has a plurality of through openings extending from a first major face at which they are engageable with respective engagement means of the first screw fixation means, to a second major face at which they are shaped to engage a boss of the second screw fixation means.

14. A bone fixation system according to claim 13 wherein the engagement means of the first screw fixation means comprise upstanding bosses.

15. A bone fixation system according to claim 13 or claim 14 wherein the second screw fixation means and the engagement means of the first screw fixation means have mutual engagement formations, and the through-openings of the cerclage receiving means are adapted to allow their mutual engagement therethrough to connect said first and second screw fixation means and said cerclage receiving means together.

16. A kit of parts for use in providing a bone fixation system according to claim 2 comprising first and second fixation means, at least some of which are elongate and have a multiplicity of engagement formations, there being a plurality of different first fixation means and/or a plurality of different second fixation means.

17. A bone fixation system according to claim 1 wherein the ladder member has means for receiving fixing screws.

18. A bone fixation system as claimed in claim 1, wherein said openings are located on said top face and said through-holes are located on said lateral edge, said top face being substantially perpendicular to said lateral edge.

19. A bone fixation system as claimed in claim 1 wherein said bottom face is curved to conform to the surface of the bone to which said system is applied.

20. A method of bone fixation comprising the steps of:
    providing cerclage cable and an elongate unitary body having a top face, a bottom face and a spaced pair of elongate side portions which define an oppositely directed pair of lateral edges, a multiplicity of spaced-apart bridge portions connecting said side portions, said bridge portions each having a pair of oppositely directed side edges shaped so that approximately rectangular openings are defined between opposed side edges of adjacent bridge portions, pairs of through-bores for cerclage cables, wherein said pairs of through-bores extend through said bridge portions, each of said bridge portions being adapted to be crimped by a crimping tool which engages said pair of oppositely directed side edges thereof;

locating said elongate unitary body so that said bottom face overlies a bone requiring fixation;

passing a length of cerclage cable around the bone and through a said pair of through-bores;

pulling the cable tight; and locking the cable in place by crimping the bridge through which said bores pass.

21. A bone fixation system comprising:

cerclage cables;

an elongate unitary body including a top face, a bottom face, a spaced pair of elongate side portions which define an oppositely directed pair of lateral edges, a multiplicity of spaced-apart bridge portions connecting said side portions, said bridge portions each having a pair of oppositely directed side edges shaped so that approximately rectangular openings are defined between opposed side edges of adjacent bridge portions, and pairs of through-bores for said cerclage cables;

wherein said pairs of through-bores extend through said bridge portions, each of said bridge portions being adapted to be crimped by a crimping tool which engages said pair of oppositely directed side edges thereof;

wherein said elongate unitary body is adapted to be located with said bottom face overlying a bone and fixed thereto by passing cerclage cable around the bone and through one of said pairs of through-bores, pulling the cable tight, and locking it in place by crimping the bridge through which said through-bores pass;

screw fixation means positioned in said approximately rectangular opening for affixing said elongate unitary body to the bone, wherein said screw fixation means, once fixed, still allows said crimping tool to crimp said bridge portion and lock said cerclage cables.

* * * * *